United States Patent
Osborne et al.

(10) Patent No.: US 11,078,482 B2
(45) Date of Patent: Aug. 3, 2021

(54) DUPLEX SEQUENCING USING DIRECT REPEAT MOLECULES

(71) Applicant: GENOME RESEARCH LIMITED, Hinxton (GB)

(72) Inventors: Robert Osborne, Great Chesterford (GB); Christopher Laumer, Cambridge (GB)

(73) Assignee: GENOME RESEARCH LIMITED, Cambridge (GB)

(*) Notice: Subject to any disclaimer, the term of this patent is extended or adjusted under 35 U.S.C. 154(b) by 0 days.

(21) Appl. No.: 16/622,838

(22) PCT Filed: Jun. 14, 2018

(86) PCT No.: PCT/IB2018/000747
§ 371 (c)(1),
(2) Date: Dec. 13, 2019

(87) PCT Pub. No.: WO2018/229547
PCT Pub. Date: Dec. 20, 2018

(65) Prior Publication Data
US 2020/0199584 A1    Jun. 25, 2020

Related U.S. Application Data

(60) Provisional application No. 62/520,184, filed on Jun. 15, 2017.

(51) Int. Cl.
*C12N 15/10* (2006.01)
*C12Q 1/6874* (2018.01)
(Continued)

(52) U.S. Cl.
CPC ....... *C12N 15/1093* (2013.01); *C12Q 1/6806* (2013.01); *C12Q 1/6869* (2013.01);
(Continued)

(58) Field of Classification Search
CPC .. C12N 15/1093; C40B 40/06; C12Q 1/6806; C12Q 1/6869; C12Q 1/6874; C12Q 1/6888
See application file for complete search history.

(56) References Cited

U.S. PATENT DOCUMENTS

2016/0362735 A1* 12/2016 Ruan ................... C12Q 1/6844

FOREIGN PATENT DOCUMENTS

EP         2792743 A1    10/2014
WO    WO 2009/089384 A1     7/2009
(Continued)

OTHER PUBLICATIONS

Schmitt et al., "Detection of ultra-rare mutations by next-generation sequencing", Proceedings of the National Academy of Sciences, 2012, vol. 109, No. 36, pp. 14508-14513.

*Primary Examiner* — Jeremy C Flinders
*Assistant Examiner* — Taryn Kimberly Wood
(74) *Attorney, Agent, or Firm* — James S. Keddie; Bozicevic, Field & Francis LLP

(57) ABSTRACT

Described herein is a population of direct repeat molecules, where each molecule of the population contains a direct repeat composed of sequences that are amplified from the opposite strands of a double-stranded fragment of genomic DNA. Within each molecule, the first repeat (referred to as TOP) is amplified from the one strand of a double-stranded fragment of genomic DNA and the second repeat (referred to as BOT') is amplified from the other strand of the same fragment of double-stranded fragment of genomic DNA.

21 Claims, 7 Drawing Sheets

Specification includes a Sequence Listing.

(51) Int. Cl.
*C12Q 1/6869* (2018.01)
*C40B 40/06* (2006.01)
*C12Q 1/6806* (2018.01)
*C12Q 1/6888* (2018.01)

(52) U.S. Cl.
CPC ............ *C12Q 1/6874* (2013.01); *C40B 40/06* (2013.01); *C12Q 1/6888* (2013.01)

(56) References Cited

FOREIGN PATENT DOCUMENTS

| WO | WO 2010/048337 A2 | 4/2010 |
| WO | WO 2011/161549 A2 | 12/2011 |
| WO | WO 2017/037656 A1 | 3/2017 |

\* cited by examiner

X       (T)TOP(A)       J       (T)BOT(A)       Y

SEQUENCE LISTING

```
<160> NUMBER OF SEQ ID NOS: 13

<210> SEQ ID NO 1
<211> LENGTH: 82
<212> TYPE: DNA
<213> ORGANISM: Artificial sequence
<220> FEATURE:
<223> OTHER INFORMATION: synthetic sequence

<400> SEQUENCE: 1
gatcggaaga gcagctacgg caaaataaag taccatcgtt agtgcgacga ccctgatcac      60
acgtgattta gatgattgtt tc                                              82
```

<210> SEQ ID NO 2
<211> LENGTH: 35
<212> TYPE: DNA
<213> ORGANISM: Artificial sequence
<220> FEATURE:
<223> OTHER INFORMATION: synthetic sequence

<400> SEQUENCE: 2
gtgactggag ttcagacgtg tacctgtcct tcctt                              35

<210> SEQ ID NO 3
<211> LENGTH: 83
<212> TYPE: DNA
<213> ORGANISM: Artificial sequence
<220> FEATURE:
<223> OTHER INFORMATION: synthetic sequence

<400> SEQUENCE: 3
aggaaggaca ggtatgaaac aatcatctaa atcacgtgtg atcagggtcg tcgcactaac     60
gatggtactt tattttgccg tag                                            83

<210> SEQ ID NO 4
<211> LENGTH: 33
<212> TYPE: DNA
<213> ORGANISM: Artificial sequence
<220> FEATURE:
<223> OTHER INFORMATION: synthetic sequence

<400> SEQUENCE: 4
acactctttc cctacacgac gctcttccga tct                                 33

<210> SEQ ID NO 5
<211> LENGTH: 16
<212> TYPE: DNA
<213> ORGANISM: Artificial sequence
<220> FEATURE:
<223> OTHER INFORMATION: synthetic sequence

<400> SEQUENCE: 5
ggggaaaatt ttcccc                                                    16

<210> SEQ ID NO 6
<211> LENGTH: 16
<212> TYPE: DNA
<213> ORGANISM: Artificial sequence
<220> FEATURE:
<223> OTHER INFORMATION: synthetic sequence

<400> SEQUENCE: 6
ggggaaaatt ttcccc                                                    16

<210> SEQ ID NO 7
<211> LENGTH: 57
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (56)..(57)
<223> OTHER INFORMATION: A phosphorothioate linkage is present between
      positions 56 and 57.

<400> SEQUENCE: 7
aatgatacgg cgaccaccga gatctacact atagcctaca ctctttccct acacgac        57

```
<210> SEQ ID NO 8
<211> LENGTH: 57
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (56)..(57)
<223> OTHER INFORMATION: A phosphorothioate linkage is present between
      positions 56 and 57.

<400> SEQUENCE: 8
aatgatacgg cgaccaccga gatctacaca tagaggcaca ctctttccct acacgac        57

<210> SEQ ID NO 9
<211> LENGTH: 57
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (56)..(57)
<223> OTHER INFORMATION: A phosphorothioate linkage is present between
      positions 56 and 57.

<400> SEQUENCE: 9
aatgatacgg cgaccaccga gatctacacc ctatcctaca ctctttccct acacgac        57

<210> SEQ ID NO 10
<211> LENGTH: 57
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (56)..(57)
<223> OTHER INFORMATION: A phosphorothioate linkage is present between
      positions 56 and 57.

<400> SEQUENCE: 10
aatgatacgg cgaccaccga gatctacacg gctctgaaca ctctttccct acacgac        57

<210> SEQ ID NO 11
<211> LENGTH: 45
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (44)..(45)
<223> OTHER INFORMATION: A phosphorothioate linkage is present between
      positions 44 and 45.

<400> SEQUENCE: 11
caagcagaag acggcatacg agatgtgact ggagttcaga cgtgt                     45

<210> SEQ ID NO 12
<211> LENGTH: 35
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (34)..(35)
<223> OTHER INFORMATION: A phosphorothioate linkage is present between
```

-continued

```
                positions 34 and 35.

<400> SEQUENCE: 12
gtgactggag ttcagacgtg tacctgtcct tcctt                              35

<210> SEQ ID NO 13
<211> LENGTH: 36
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (35)..(36)
<223> OTHER INFORMATION: A phosphorothioate linkage is present between
      positions 35 and 36.

<400> SEQUENCE: 13
atgaaacaat catctaaatc acgtgtgatc agggtc                             36
```

DUPLEX SEQUENCING USING DIRECT REPEAT MOLECULES

CROSS-REFERENCING

This application is a § 371 national phase of International Application No. PCT/IB2018/000747, filed on Jun. 14, 2018, which claims the benefit of U.S. provisional application Ser. No. 62/520,184, filed on Jun. 15, 2017, which applications are incorporated herein by reference.

BACKGROUND

Many diseases are caused by somatic mutations. Because somatic mutations only occur in a fraction of the cells in the body, they can be very difficult to detect by next generation sequencing (NGS). One problem is that every library preparation method and sequencing platform results in sequence reads that contain errors, e.g., PCR errors and sequencing errors. While it is sometimes possible to correct systematic errors (e.g., those that are correlated with known parameters including sequencing cycle-number, strand, sequence-context and base substitution probabilities), it is often impossible to figure out with any certainty whether a variation in a sequence is caused by an error or if it is a "real" mutation. This problem is exacerbated if the amount of sample is limited and mutation-containing polynucleotides are present only at relatively low levels, e.g., less than 5%, in the sample. For example, if a sample contains only one copy of a mutation-containing polynucleotide in a background of hundreds of polynucleotides that are otherwise identical to the mutation-containing polynucleotide except that they do not contain the mutation, then, after those polynucleotides have been sequenced, it is often impossible to tell whether the variation (which may only be observed in about 1 in ≥one hundred of the sequence reads) is an error that occurred during amplification or sequencing. Thus, the detection of somatic mutations that cause diseases can be extremely difficult to detect with any certainty.

This problem is exacerbated by that fact that DNA is often damaged prior to or during library construction. For example, deaminated cytosines and oxidixized guanines both base pair with adenine, which lead to erroneous base calls after amplification. It has been found that damaged nucleotides are a pervasive cause of sequencing errors and this, in turn, confounds variant identification (see, e.g., Chen et al Science 2017 355:752-756). In these studies, the authors found that DNA damage accounts for the majority of the erroneous identification of variants with low to moderate (1 to 5%) frequency. As damage affects only one base of a pair, damaged nucleotides could, in theory, be identified by analyzing both strands of the damaged DNA molecule. Sequencing methods that allow a comparison of the top and bottom strands of an original double-stranded molecule of genomic DNA (i.e., a fragment in a sample) are referred to as "duplex sequencing" methods.

Schmitt et al (Proc. Natl. Acad. Sci. 2012 109: 14508-14513) proposed a solution that involves tagging a sample with custom Y-shaped adaptors. The Y-shaped adaptors were generated by first introducing a single-stranded randomized nucleotide sequence into the stem region of one adaptor strand. A second adaptor strand, is then extended using a DNA polymerase, to generate a Y-shaped adaptor where the stem region has a complementary double-stranded randomized nucleotide sequence. Adaptors are then tailed by adding a 3' base overhang using a DNA polymerase. The overhang assists in adaptor ligation to fragmented DNA tailed with a complementary base. Adaptors are ligated to fragmented DNA before the library is PCR amplified, using primers that hybridize to the single stranded (non-stem) region of the adaptors. Tag sequences allow reads deriving from the top strands of fragmented DNA to be discriminated from sequence reads derived from bottom strands. This requires paired-end sequencing and comparison of both read 1 and read 2 tag sequences.

While useful for discriminating between sequence reads from top and bottom strands, Schmitt's method has several limitations.

First, because sequence tags are random it can be difficult to identify tags that have been 'mutated' due to PCR or sequencing errors. In addition, it is difficult to detect errors that occurred during oligonucleotide synthesis, such as n−1 deletions.

Second, manufacture of the double-stranded adaptors is complex and expensive. Typically, Y-shaped adaptors are manufactured by annealing two oligonucleotides. In contrast, Schmitt's method also includes incorporation of random bases into the oligonucleotide, DNA polymerase extension and tailing different 3' bases onto adaptors and fragmented DNA. These steps can be inefficient and require additional purification and quality control checks.

Third, it is difficult to control the relative incorporation of different bases in the degenerate tag sequence during oligonucleotide synthesis. This can result in some tag sequences being present at higher levels than others in the pool of Y-shaped adaptors, which reduces the probability that a fragment is tagged with unique tag sequences.

Fourth, because the tags are attached to the template in bulk, a number of tag sequences are required to reduce the probability of different fragments being attached to adaptors containing the same tag sequences and to improve the chance of detecting a PCR and/or sequencing error that results in one tag being 'mutated' into another. As a result, the tag sequences are typically relatively long; for example, Schmitt use 12 nucleotide tag sequences. However, long runs of random bases are likely to form intra- and inter-molecular hybrids, which can cause problems for downstream applications such as in-solution hybridization. In this application, adaptor and index sequences are 'masked' to reduce the effect of inter-molecular hybridisation by including blocking oligonucleotides in the hybridization. However, masking the degenerate region of the tag requires incorporation of 'universal' bases such as inosine, with associated additional costs. In addition, tag sequences use up a proportion of each sequencing read thereby reducing the sequence data from target fragment(s). This effect is increased if tag sequences are longer.

Fifth, in the Schmitt protocol the PCR is performed on a pool of molecules, each tagged with different 5' and 3' random tag sequences. Failure to remove residual adaptors can result in hybridization of an adaptor strand to a template molecule during PCR, which can inadvertently tag a molecule with a different tag sequence.

Sixth, Schmitt tag DNA fragments with both 5' and 3' random tag sequences. If, by chance, the 5' and 3' tag sequences are complementary, or partially complementary, then the tags can intra-molecularly hybridize resulting in suppression of PCR amplification. This can result in uneven amplification of template molecules, depending on their 5' and 3' tag combination.

Finally, in the Schmitt protocol both strands of the original double-stranded molecule are amplified on separate molecules. The protocol relies on sampling sufficient sequencing reads from each strand to generate consensus sequences. If n reads are required to form a single-strand consensus then the minimum number of reads is 2n. In practice, the number of reads of each strand often varies, depends on the depth of sequencing, the capacity of the sequencer and the number of double-stranded template molecules in the library. This means that libraries require careful quantitation to achieve the desired molecular complexity in order to maximize the recovery of duplex sequences.

The present disclosure provides an alternative, better, way for sequencing the top and bottom strands of a double-stranded fragment of genomic DNA.

SUMMARY

Described herein is a population of direct repeat molecules, where each molecule of the population contains a direct repeat composed of sequences that are amplified from the opposite strands of a double-stranded fragment of genomic DNA. Within each molecule, the first repeat (referred to as TOP) is amplified from the one strand of a double-stranded fragment of genomic DNA and the second repeat (referred to as BOT') is amplified from the other strand of the same fragment of double-stranded fragment of genomic DNA. Within each molecule, the sequences of TOP and BOT' are often the same. However, in cases where there is damage in the original molecule, the sequences of TOP and BOT' (within a single molecule) may differ. As such, within each repeat molecule, TOP and BOT' are typically identical except for: positions that correspond to (a) damaged nucleotides in the double-stranded fragment of genomic DNA from which those strands were copied or (b) errors that occur during amplification of the direct repeat molecule (e.g., nucleotides that are mis-incorporated or deletions caused by a stutter or slippage event during amplification). TOP and BOT' are typically at least 95% identical. The molecules can be sequenced to obtain the sequences of TOP and BOT' from the same direct repeat molecule. The TOP and BOT' from the same direct repeat molecule can be compared determine if they are the same or different. If the sequences are different, the method may comprise excluding the base calls corresponding to a sequence difference from future analysis. The method may be used to identify damaged nucleotides and amplification errors, as well as sequencing errors (i.e., errors that stem from the sequence reaction itself, not in the sequencing template).

The method finds particular use in analyzing samples of DNA that contain damaged DNA, samples in which the amount of DNA is limited and/or samples that contain fragments having a low copy number mutation (e.g. a sequence caused by a mutation that is present at low copy number relative to sequences that do not contain the mutation). These features are often present in patient samples that can be obtained non-invasively, e.g., circulating tumor (ctDNA) samples, which can obtained from peripheral blood, or invasively, e.g., tissue sections. In some embodiments, the sample may be DNA obtained from tissue embedded in paraffin (i.e., an FFPE sample). In such samples, the mutant sequences may only be present at a very limited copy number (e.g., less than 10, less than 5 copies or even 1 copy in a background of hundreds or thousands of copies of the wild type sequence). In these situations, without an effective way to eliminate errors generated by DNA damage, it can be almost impossible to identify a true sequence variation with significant confidence.

In theory, a single duplex molecule could be converted into an inverted repeat molecule, for example by ligation of a hairpin adaptor to one terminus. Sequencing both strands of the inverted repeat molecule would also generate sequence data from both strands of the original template molecule. However, forming inverted repeat molecules is inefficient. For example, if using a Y-stem and a hairpin adaptor at most only ~50% of the tagged molecules are subsequently amplifiable. In addition, PCR amplification and bridge amplification during sequencing is inefficient owing to the propensity for hairpin sequences to refold.

The present method, depending on how it is implemented, may have multiple advantages over the prior methods, e.g., the Schmitt method summarized above. Duplex and, the recently described, bottleneck sequencing are capable of specific detection of somatic variants on a genome-wide scale (Hoang et al. Genome-wide quantification of rare somatic mutations in normal human tissues using massively parallel sequencing. Proc Natl Acad Sci USA 113, 9846-51 (2016); Schmitt et al. Detection of ultra-rare mutations by next-generation sequencing. Proc Natl Acad Sci USA 109, 14508-13 (2012). Both methods rely on error-correction by sampling duplicate reads that derive from one strand of an original duplex, followed by error-detection by comparing the two single-strand consensus sequences (SSCSs) to generate a duplex consensus sequence (DCS). Assuming that three duplicate reads are required for both strands, the maximum rate of information transfer is 1/6. In reality, the number of reads for each strand follows an approximately negative binomial distribution and we do not always recovery both strands from one molecule in the sequencing data. The current method increase the rate of information transfer. Each amplicon contains two insert sequences in a direct-repeat orientation (FIG. 7). One insert derives from the original Watson strand, and the other from the original Crick strand of a single double-stranded molecule. A DCS can be formed for each molecule by comparing reads deriving from both direct-repeats. This gives an effective rate of 1/1 i.e. every read can form a DCS. For detection of somatic variants on a genome-wide scale it is likely that we will also need to sample duplicate reads, so the maximum rate of information transfer is 1/2 or 1/3, a 2-3 fold decrease in the amount of sequencing required.

BRIEF DESCRIPTION OF THE DRAWINGS

The invention is best understood from the following detailed description when read in conjunction with the accompanying drawings. It is emphasized that, according to common practice, the various features of the drawings are not to scale. Indeed, the dimensions of the various features are arbitrarily expanded or reduced for clarity. Included in the drawings are the following figures.

FIG. 5 schematically illustrates another method by which a population of direct repeat molecules can be produced. Adaptor tagging using 2× types of adaptor (maximum 50% molecules tagged) R1/R2=read1/2, J/J'=junction. Emulsion PCR with primers R1/R2 in excess. Small amount of primers J/J' to help initiate the reaction. This method may have the following features: one starting fragment per microdroplet, a fragment length<2× read length, all molecules are duplex sequenced, size selection to select double-wide fragments from R1/J' or R2/J products. R1/R1 or R2/R2 molecules will be subject to suppression PCR; and bulk emPCR required to create a sufficiently diverse library (rather than monodisperse microdroplets from e.g. QX100/200)

Figure 5:
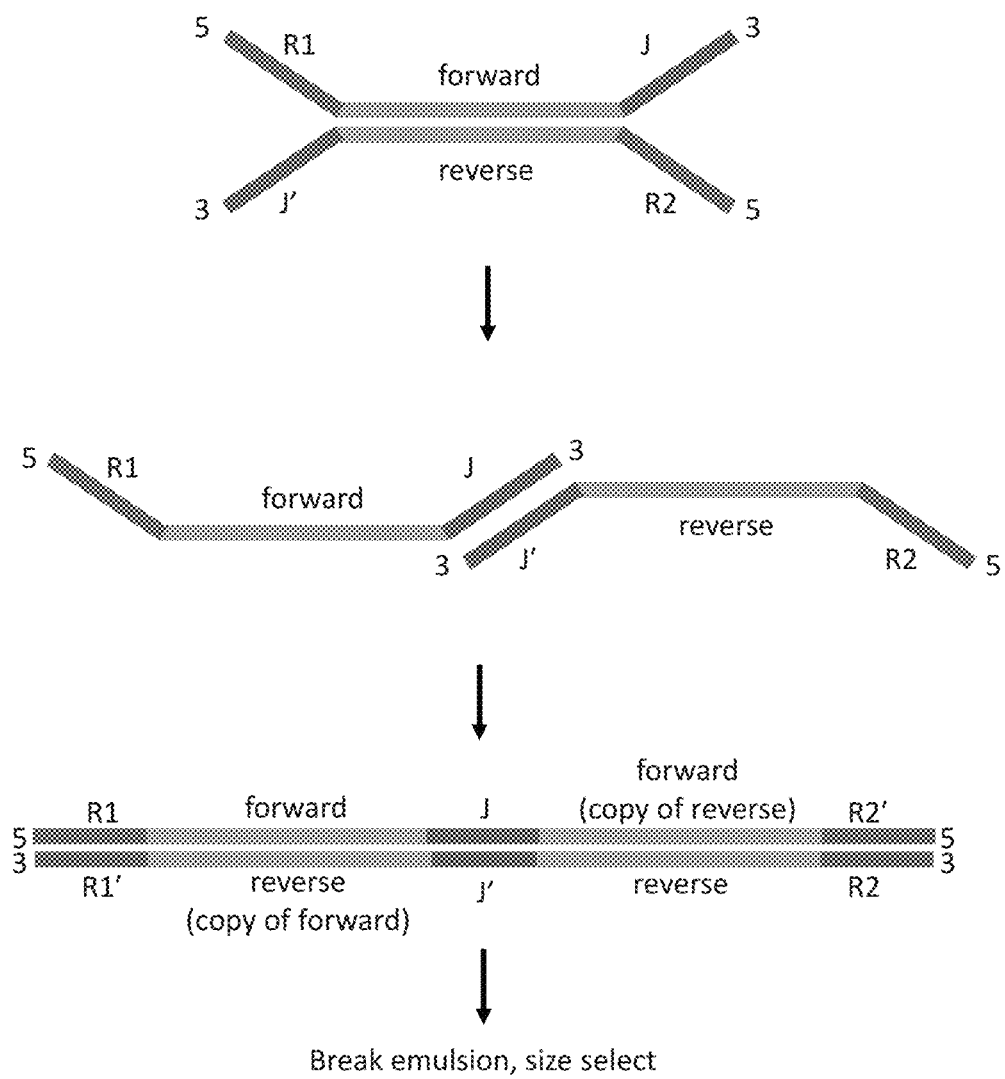
Figure 6:
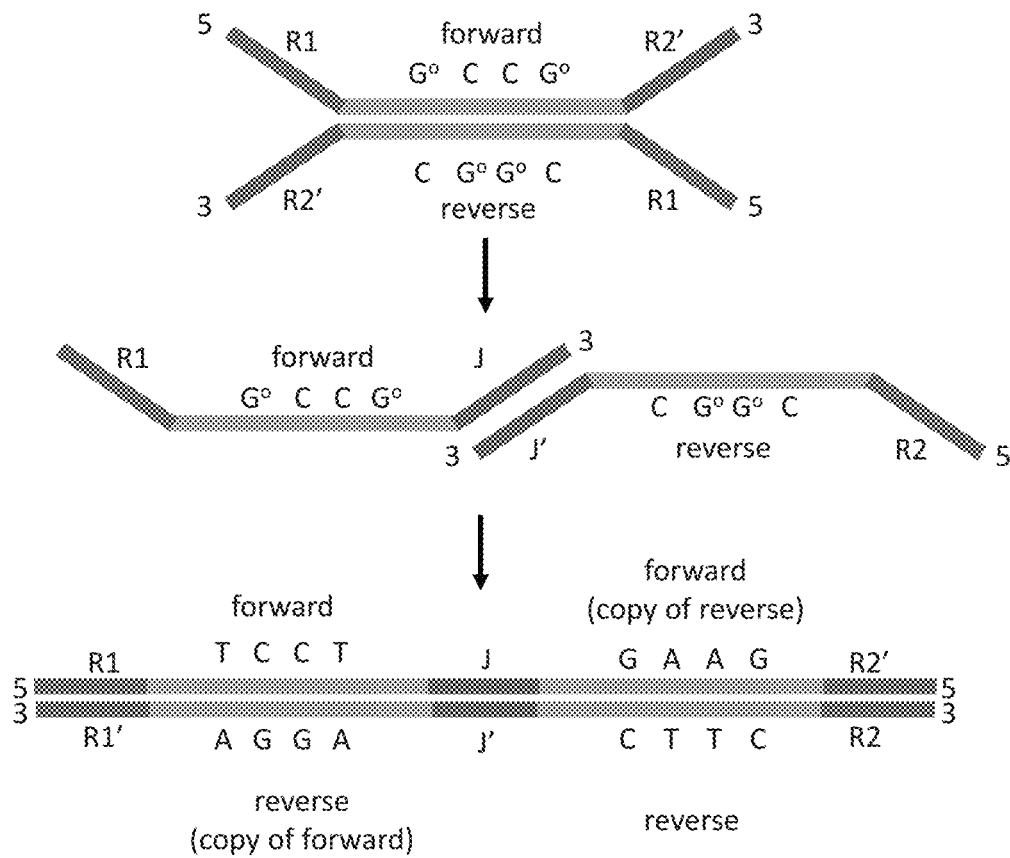

FIG. 6 schematically illustrates how a damaged nucleotide)(G° can be identified using the method illustrated in FIG. 5.

Figures 7, 8:
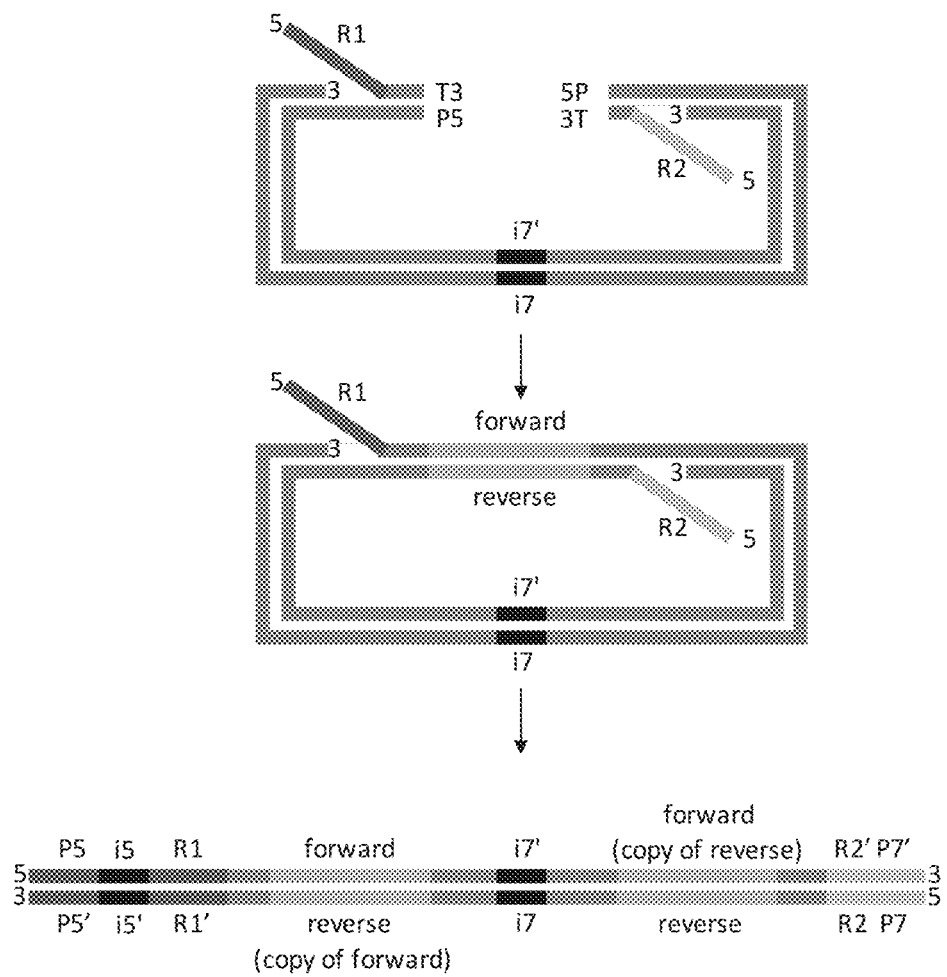

FIG. 7 schematically illustrates an embodiment of the method, which may be referred to as "direct repeat sequencing" or "DRSeq" for short. Adaptor sequence contains blue read 1 (R1) and yellow read 2 (R2). 5P is a 5' phosphate. 3-OH-T is a 3' T overhang with a hydroxyl group. The adaptor is ligated to an A-tailed genomic DNA insert, shown in grey, at low concentration to favour circularisation over concatenation. After ligation, a strand-displacing DNA polymerase is used to generate the double-stranded amplicon, which is then amplified by PCR. The i7 index sequence is within the adaptor sequence, whereas the i5 index sequence is introduced on a P5-i5-R1 PCR primer.

FIG. 8 shows an exemplary adaptor sequence. Blue is read 1, yellow read 2, green, with black text, inner-stem region 1 and green, with red text, inner-stem region 2. Both termini have a 5' phosphate and a 3' dT overhang. (SEQ ID NOS: 1-4).

Figure 9:
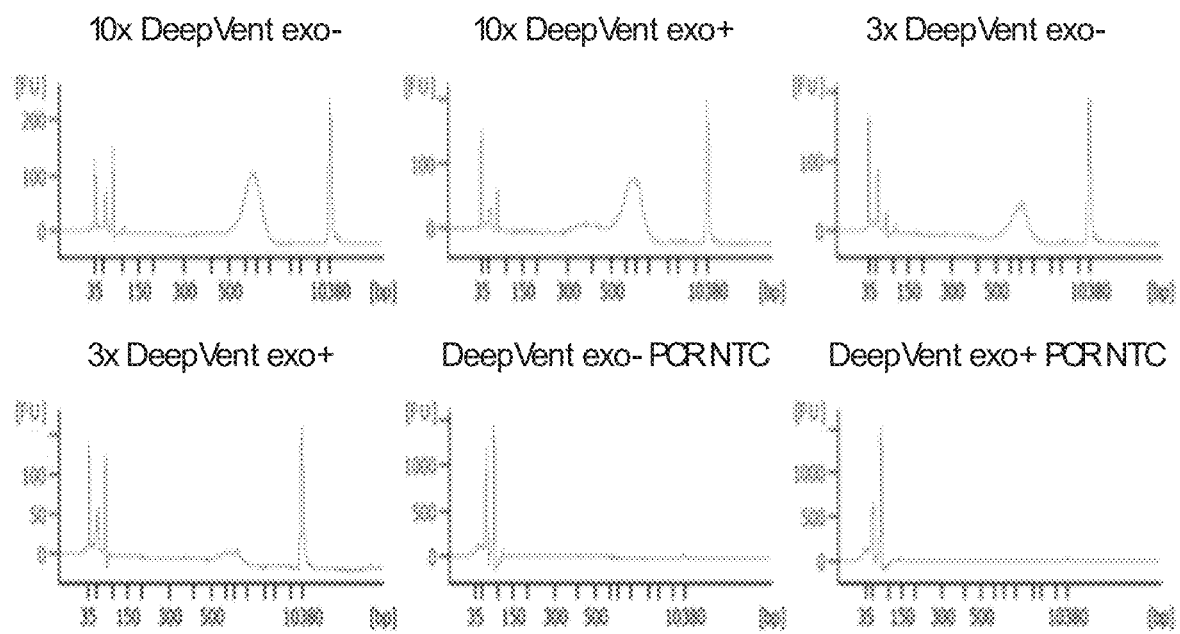

FIG. 9 shows Bioanalyzer traces.

Figure 10:
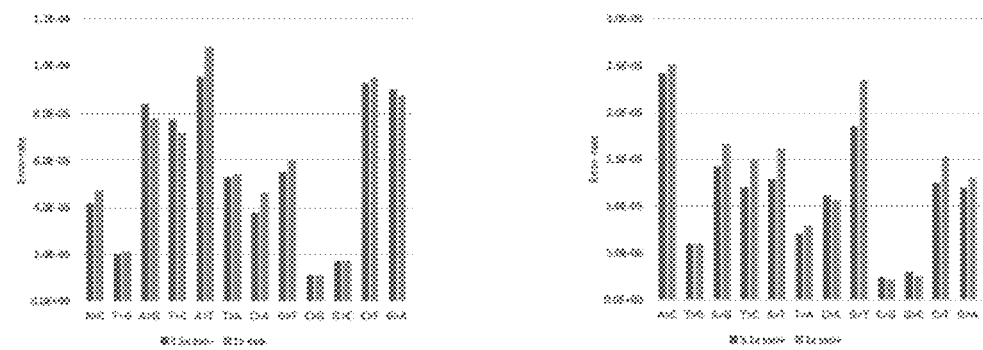

FIG. 10 shows the error profiles for DeepVent exo− (left panel) and DeepVent exo+ (right panel). The y axis in the graphs are different scales.

DEFINITIONS

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "sample" as used herein relates to a material or mixture of materials, typically containing one or more analytes of interest. In one embodiment, the term as used in its broadest sense, refers to any plant, animal, microbial or viral material containing genomic DNA, such as, for example, tissue or fluid isolated from an individual (including without limitation plasma, serum, cerebrospinal fluid, lymph, tears, saliva and tissue sections) or from in vitro cell culture constituents, as well as samples from the environment.

The term "nucleic acid sample," as used herein, denotes a sample containing nucleic acids. Nucleic acid samples used herein may be complex in that they contain multiple different molecules that contain sequences. Genomic DNA samples from a mammal (e.g., mouse or human) are types of complex samples. Complex samples may have more than about $10^4$, $10^5$, $10^6$ or $10^7$, $10^8$, $10^9$ or $10^{10}$ different nucleic acid molecules. A DNA target may originate from any source such as genomic DNA, or an artificial DNA construct. Any sample containing nucleic acid, e.g., genomic DNA from tissue culture cells or a sample of tissue, may be employed herein.

The term "mixture" as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "nucleotide" is intended to include those moieties that can be copied using a polymerase. Nucleotides contain not only the known purine and pyrimidine bases, but also other heterocyclic bases that have been modified e.g., "damaged" bases that have oxidized or deadenylated for example. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, greater than 10,000 bases, greater than 100,000 bases, greater than about 1,000,000, up to about $10^{10}$ or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylenecarbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid," or "UNA," is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, or both ribonucleotide monomers and deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually in the range of between 8 to 100 nucleotides in length, such as 10 to 75, 15 to 60, 15 to 40, 18 to 30, 20 to 40, 21 to 50, 22 to 45, 25 to 40, and so on. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length. In some embodiments a primer can be activated prior to primer extension. For example, some primers have a 3' block and internal RNA base. The RNA base can be removed by RNaseH or another treatment, thereby producing a 3' hydroxyl group which can be extended. Other methods for activating primers exist.

Primers are usually single-stranded for maximum efficiency in amplification, but may alternatively be double-stranded or partially double-stranded. If double-stranded, the primer is usually first treated to separate its strands before being used to prepare extension products. This denaturation step is typically effected by heat, but may alternatively be carried out using alkali, followed by neutralization. Also included in this definition are toehold exchange primers, as described in Zhang et al (Nature Chemistry 2012 4: 208-214), which is incorporated by reference herein.

Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The term "hybridization" or "hybridizes" refers to a process in which a region of nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strand region in a hybridization reaction. The hybridization reaction can be made to be highly specific by adjustment of the hybridization conditions (often referred to as hybridization stringency) under which the hybridization reaction takes place, such that two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

The term "amplifying" as used herein refers to the process of synthesizing nucleic acid molecules that are complementary to one or both strands of a template nucleic acid. Amplifying a nucleic acid molecule may include denaturing the template nucleic acid, annealing primers to the template nucleic acid at a temperature that is below the melting temperatures of the primers, and enzymatically elongating from the primers to generate an amplification product. The denaturing, annealing and elongating steps each can be performed one or more times. In certain cases, the denaturing, annealing and elongating steps are performed multiple times such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acids, which are produced from the amplifying process as defined herein.

The terms "determining," "measuring," "evaluating," "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "ligating," as used herein, refers to the enzymatically catalyzed joining of the terminal nucleotide at the 5' end of a first DNA molecule to the terminal nucleotide at the 3' end of a second DNA molecule.

A "plurality" contains at least 2 members. In certain cases, a plurality may have at least 2, at least 5, at least 10, at least 100, at least 1000, at least 10,000, at least 100,000, at least $10^6$, at least $10^7$, at least $10^8$ or at least $10^9$ or more members.

An "oligonucleotide binding site" refers to a site to which an oligonucleotide hybridizes in a target polynucleotide. If an oligonucleotide "provides" a binding site for a primer, then the primer may hybridize to that oligonucleotide or its complement.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "Watson" (or "TOP") and "Crick" (or "BOT") strands. In certain cases, complementary strands of a chromosomal region may be referred to as "plus" and "minus" strands, the "first" and "second" strands, the "coding" and "noncoding" strands, the "top" and "top" strands or the "sense" and "antisense" strands. The assignment of a strand as being a Watson (or "TOP") or Crick (or BOT) strand is arbitrary and does not imply any particular orientation, function or structure.

The term "extending", as used herein, refers to the extension of a primer by the addition of nucleotides using a polymerase. If a primer that is annealed to a nucleic acid is extended, the nucleic acid acts as a template for extension reaction.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

The terms "next-generation sequencing" or "high-throughput sequencing", as used herein, refer to the so-called parallelized sequencing-by-synthesis or sequencing-by-ligation platforms currently employed by Illumina, Life Technologies, and Roche, etc. Next-generation sequencing methods may also include nanopore sequencing methods such as that commercialized by Oxford Nanopore Technologies, electronic-detection based methods such as Ion Torrent technology commercialized by Life Technologies, or single-molecule fluorescence-based methods such as that commercialized by Pacific Biosciences.

The term "barcode sequence" or "molecular barcode", as used herein, refers to a unique sequence of nucleotides can be used to a) identify and/or track the source of a polynucleotide in a reaction, b) count how many times an initial molecule is sequenced and c) pair sequence reads from different strands of the same molecule. Barcode sequences may vary widely in size and composition; the following references provide guidance for selecting sets of barcode sequences appropriate for particular embodiments: Casbon (Nuc. Acids Res. 2011, 22 e81), Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 2 to 36 nucleotides, or from 6 to 30 nucleotides, or from 8 to 20 nucleotides.

In some cases, a barcode may contain a "degenerate base region" or "DBR", where the terms "degenerate base region" and "DBR" refers to a type of molecular barcode that has complexity that is sufficient to help one distinguish between fragments to which the DBR has been added. In some cases, substantially every tagged fragment may have a different DBR sequence. In these embodiments, a high complexity DBR may be used (e.g., one that is composed of at least 10,000 or 100,000, or more sequences). In other embodiments, some fragments may be tagged with the same DBR sequence, but those fragments can still be distinguished by the combination of i. the DBR sequence, ii. the sequence of the fragment, iii. the sequence of the ends of the fragment, and/or iv. the site of insertion of the DBR into the fragment. In some embodiments, at least 95%, e.g., at least 96%, at least 97%, at least 98%, at least 99% or at least 99.5% of the target polynucleotides become associated with a different DBR sequence. In some embodiments a DBR may comprise one or more (e.g., at least 2, at least 3, at least 4, at least 5, or 5 to 30 or more) nucleotides selected from R, Y, S, W, K, M, B, D, H, V, N (as defined by the IUPAC code). In some cases, a double-stranded barcode can be made by making an oligonucleotide containing degenerate sequence (e.g., an oligonucleotide that has a run of 2-10 or more "Ns") and then copying the complement of the barcode onto the other strand, as described below.

Oligonucleotides that contain a variable sequence, e.g., a DBR, can be made by making a number of oligonucleotides separately, mixing the oligonucleotides together, and by amplifying them en masse. In other words, the population of oligonucleotides that contain a variable sequence can be made as a single oligonucleotide that contains degenerate positions (i.e., positions that contain more than one type of nucleotide). Alternatively, such a population of oligonucleotides can be made by fabricating them individually or using an array of the oligonucleotides using in situ synthesis methods, cleaving the oligonucleotides from the substrate and optionally amplifying them. Examples of such methods are described in, e.g., Cleary et al (Nature Methods 2004 1: 241-248) and LeProust et al (Nucleic Acids Research 2010 38: 2522-2540).

In some cases, a barcode may be error correcting. Descriptions of exemplary error identifying (or error correcting) sequences can be found throughout the literature (e.g., in are described in US patent application publications US2010/0323348 and US2009/0105959 both incorporated herein by reference). Error-correctable codes may be necessary for quantitating absolute numbers of molecules. Many reports in the literature use codes that were originally developed for error-correction of binary systems (Hamming codes, Reed Solomon codes etc.) or apply these to quaternary systems (e.g. quaternary Hamming codes; see Generalized DNA barcode design based on Hamming codes, Bystrykh 2012 PLoS One. 2012 7: e36852).

In some embodiments, a barcode may additionally be used to determine the number of initial target polynucleotide molecules that have been analyzed, i.e., to "count" the number of initial target polynucleotide molecules that have been analyzed. PCR amplification of molecules that have been tagged with a barcode can result in multiple sub-populations of products that are clonally-related in that each of the different sub-populations is amplified from a single tagged molecule. As would be apparent, even though there may be several thousand or millions or more of molecules in any of the clonally-related sub-populations of PCR products and the number of target molecules in those clonally-related sub-populations may vary greatly, the number of molecules tagged in the first step of the method can be estimated by counting the number of DBR sequences associated with a target sequence that is represented in the population of PCR products. This number is useful because, in certain embodiments, the population of PCR products made using this method may be sequenced to produce a plurality of sequences. The number of different barcode sequences that are associated with the sequences of a target polynucleotide can be counted, and this number can be used (along with, e.g., the sequence of the fragment, the sequence of the ends of the fragment, and/or the site of insertion of the DBR into the fragment) to estimate the number of initial template nucleic acid molecules that have been sequenced. Such tags can also be useful in correcting sequencing errors.

The terms "sample identifier sequence" or "sample index" refer to a type of barcode that can be appended to a target polynucleotide, where the sequence identifies the source of the target polynucleotide (i.e., the sample from which sample the target polynucleotide is derived). In use, each sample is tagged with a different sample identifier sequence (e.g., one sequence is appended to each sample, where the different samples are appended to different sequences), and the tagged samples are pooled. After the pooled sample is sequenced, the sample identifier sequence can be used to identify the source of the sequences.

The term "adaptor" refers to a nucleic acid that can be joined to at least one strand of a double-stranded DNA molecule. The term "adaptor" refers to molecules that are at least partially double-stranded. An adaptor may be 20 to 150 bases in length, e.g., 40 to 120 bases, although adaptors outside of this range are envisioned.

The term "adaptor-tagged," as used herein, refers to a nucleic acid that has been tagged by, i.e., covalently linked with, an adaptor. An adaptor can be joined to a 5' end and/or a 3' end of a nucleic acid molecule.

The term "tagged DNA" as used herein refers to DNA molecules that have an added adaptor sequence, i.e., a "tag" of synthetic origin. An adaptor sequence can be added (i.e., "appended") by ligation.

The term "complexity" refers the total number of different sequences in a population. For example, if a population has 4 different sequences then that population has a complexity of 4. A population may have a complexity of at least 4, at least 8, at least 16, at least 100, at least 1,000, at least 10,000 or at least 100,000 or more, depending on the desired result.

The term "of the formula" means that the individual molecules in a population are described by, i.e., encompassed by, the formula.

Certain polynucleotides described herein may be referred by a formula (e.g., "X-TOP-J-BOT'-Y"). Unless otherwise indicated the polynucleotides defined by a formula are oriented in the 5' to 3' direction. The components of the formula, e.g., "X", "TOP", etc., refer to separately definable sequences of nucleotides within a polynucleotide, where, unless implicit from the context, the sequences are linked together covalently such that a polynucleotide described by a formula is a single molecule. In some cases the components of the formula are immediately adjacent to one another in the single molecule. Unless otherwise indicated or implicit from the context, a region defined by a formula (e.g., TOP, J or BOT') may have additional sequence, a primer binding site, a molecular barcode, a promoter, or a spacer, etc., at its 3' end, its 5' end or both the 3' and 5' ends. As would be apparent, the various component sequences of a polynucleotide (e.g., X, Y, TOP, J or BOT' etc.,) may independently be of any desired length as long as they capable of performing the desired function (e.g., hybridization to another sequence). For example, the various component sequences of a polynucleotide may independently have a length in the range of 8-80 nucleotides, e.g., 10-50 nucleotides or 12-30 nucleotides.

The term "opposite strands", as used herein, refers to the top and bottom strands, where the strands are complementary to one another, except for damaged nucleotides.

The term "potential sequence variation", as used herein, refers to a sequence variation, e.g., a substitution, deletion, insertion or rearrangement of one or more nucleotides in one sequence relative to another.

The term "amplification error" refers to a mis-incorporated base, or a deletion/insertion caused by polymerase stutter. Stutter usually occurs in repeat sequences, e.g., short tandem repeats (STRs) or microsatellite repeats and is presumed to be due to miscopying or slippage by the polymerase The term "target enrichment", as used herein, refers to a method in which selected sequences are separated from other sequences in a sample. This may be done by hybridization to a probe, e.g., hybridizing a biotinylated oligonucleotide to the sample to produce duplexes between the oligonucleotide and the target sequence, immobilizing the duplexes via the biotin group, washing the immobilized duplexes, and then releasing the target sequences from the oligonucleotides. Alternatively, a selected sequence may be enriched by amplifying that sequence, e.g., by PCR using one or more primers that hybridize to a site that is proximal to the target sequence.

The terms "minority variant" and "sequence variation", as used herein, is a variant that is present a frequency of less than 50%, relative to other molecules in the sample. In some cases, a minority variant may be a first allele of a polymorphic target sequence, where, in a sample, the ratio of molecules that contain the first allele of the polymorphic target sequence compared to molecules that contain other alleles of the polymorphic target sequence is 1:100 or less, 1:1,000 or less, 1:10,000 or less, 1:100,000 or less or 1:1,000,000 or less.

The term "duplex sequencing" refers to a method in which sequences for both strands of a double-stranded molecule of genomic DNA are obtained. In duplex sequencing, the sequences derived from the top strand of double-stranded molecule of genomic DNA are distinguishable from sequences derived from the bottom strand of that molecule in such a way that the sequences for the top and bottom strands from the same double-stranded molecule of genomic DNA can be compared.

The term "direct repeat" refers a molecule that contains two copies of near identical sequences, i.e., sequences that of the same length and that are at least 95% identical in nucleotide sequence.

For ease of reference, the reverse complement of a sequence is indicated by the prime ("'") symbol. For example, the reverse complement of a sequence referred to as "BOT" is may be referred to as "BOT'".

Other definitions of terms may appear throughout the specification.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a nucleic acid" includes a plurality of such nucleic acids and reference to "the compound" includes reference to one or more compounds and equivalents thereof known to those skilled in the art, and so forth.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, A., *Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figures 1, 2:
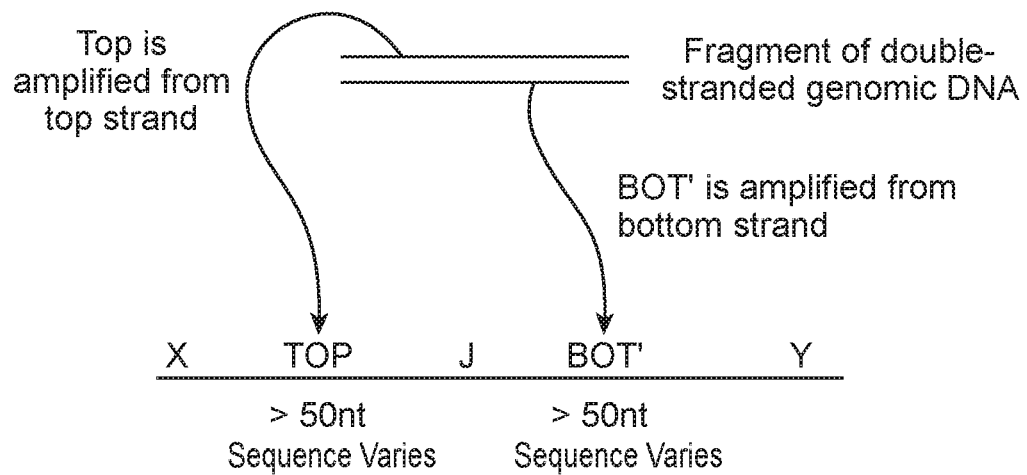
FIG. 1 schematically illustrates some of the elements of a population of direct repeat molecules.
FIG. 2 schematically illustrates a population of direct repeat molecules that have been A-tailed prior to ligation to an adaptor.

Provided herein, among other things, is a population of direct repeat molecules. In some embodiments the population of direct repeat molecules have a strand of the formula: 5'-X-TOP-J-BOT'-Y-3'. An example of such a population of direct repeat is illustrated in FIG. 1. As shown, within each repeat molecule the TOP and BOT' regions are amplified from opposite strands of a fragment of double-stranded genomic DNA. TOP has the same or a very similar sequence as one strand (the top strand of the fragment, for example) of a fragment of double-stranded genomic DNA whereas BOT' has the same or a very similar sequence as the reverse complement of other strand of the fragment (e.g., the bottom strand of the fragment). The TOP and BOT' sequences should be identical except for nucleotides that correspond to (i.e., are at a position that corresponds to the position of) damaged nucleotides in the fragment of double-stranded genomic DNA or errors that have occurred during amplification.

A "damaged nucleotide" refers to any derivative of adenine, cytosine, guanine, and thymine that has been altered in a way that allows it to pair with a different base. In non-damaged DNA, A base pairs with T and C base pairs with G. However, some bases can be oxidized, alkylated or deaminated in a way that effects base pairing. For example, 7,8-dihydro-8-oxoguanine (8-oxo-dG) is a derivative of guanine that base pairs with adenine instead of cytosine. This derivative causes a G to T transversion after replication. Deamination of cytosine produces uracil, which can base pair with adenine, leading to a C to T change after replication. Other examples or damaged nucleotide that are capable of mismatched pairing include are known.

Within a molecule, the sequences of TOP and BOT' have identical lengths and are at least 95% identical (e.g., at least 95% identical, at least 96% identical, at least 97% identical, at least 98% identical, at least 99% identical or 100% identical, depending on the extent of DNA damage in the fragment of double-stranded genomic DNA and/or amplification errors) and, with the exception of nucleotides that correspond to damage nucleotides and amplification errors, should be identical. As shown, the molecules have a unit length of 1, meaning that there is only one copy of TOP and one copy of BOT' in each molecule. Within the population, the sequence of TOP varies and may have a median length of at least 50 nucleotides. Within the population, the complexity and median length of the sequence of BOT' varies is approximately the same as the complexity and median length of the sequence of TOP, since those sequences are almost identical. In the population, TOP and BOT' each have a complexity of at least $10^3$, e.g., at least $10^4$, at least $10^5$, at least $10^6$ or at least $10^7$, at least $10^8$, at least $10^9$ or at least $10^{10}$, for example, meaning that in the population, region TOP and BOT' are represented by at least $10^3$ different sequences. The lengths of TOP and BOT' generally depends on the lengths of the fragments of genomic DNA in the sample from which the molecules are made. In some embodiments, the fragments may have a median size that no more than 2 kb in length (e.g., in the range of 50 bp to 2 kb, e.g., 75 bp to 1.5 kb, or 100 bp to 1 kb). The lengths of the fragments may be tailored to the sequencing platform being used.

As shown, X and Y are different, non-complementary sequences of at least 10 nucleotides (e.g., at least 10, 12 or 14 nucleotides in length) that do not vary in the population. The X and Y sequences allows the entire population of fragments to be amplified by a single pair of primers: a first primer that hybridizes to Y and another that hybridizes to the complement of X or a first primer that hybridizes to the complement of Y and another that hybridizes to X. X and Y do not need to be at the very end of a molecule although, in many embodiments, X and Y are within 50 nt, e.g., within 30 nt of the end of molecule. J is a junction sequence of, e.g., at least 2 nucleotides (e.g., at least 10 or 10 to 100 nt). The sequences of X and Y may be compatible with the sequencing platform being used. The sequence of J may vary in the population. The molecules of a population of direct repeat molecules may be single-stranded or double-stranded. The molecules may be free in solution (i.e., untethered) or, in some embodiments, the molecules may be tethered to a support via a covalent or non-covalent linkage.

In some embodiments, each molecule in the population may contain a molecular barcode, e.g., a sample identifier or degenerate base region. In these embodiments, the barcode may be between X and TOP, between TOP and J, in J, between J and BOT' or between BOT' and Y. As noted above, a molecular barcode may have a length of 2-30 nucleotides, e.g., 4-15 nucleotides and may have a complexity of at least 4, e.g., a complexity of at least 16 or more.

In some embodiments, and as shown in FIG. 2, the population of direct repeat molecules have a strand of the formula: X-(T)TOP(A)-J-(T)BOT'(A)-Y, wherein (T) and (A) are thymine and adenine nucleotides that are immediately adjacent to the TOP and BOT' sequences in the direct repeat molecule. These nucleotides may have been added if the fragments of double-stranded genomic DNA are polished and A-tailed prior to addition of a T-tailed adaptor.

As noted above, TOP and BOT' are copied from fragments of double-stranded DNA genomic DNA. The genomic DNA may be eukaryotic genomic DNA, e.g., mammalian genomic DNA that isolated from a tissue biopsy or cell-free DNA (cfDNA), microbial genomic DNA or viral genomic DNA, for example.

The population of population of direct repeat molecules may be sequenced. These embodiments may comprise sequencing the population of direct repeat molecules to obtain the sequences of TOP and BOT' from the same molecule (i.e., including reverse complements of the same) and comparing the sequences of TOP and BOT' from the same molecule to determine if they are the same or different. This step can be done by aligning the TOP sequence with the BOT' sequence, or aligning the reverse complement of the TOP sequence with the BOT' sequence, aligning the TOP sequence with the complement of the BOT' sequence, or by aligning the reverse complement of the TOP sequence with the reverse complement of the BOT' sequence. In some embodiments, the comparison step may result in the identification of a difference in the sequences of TOP and BOT' from the same molecule. If a difference is detected, the base call corresponding to that position of that difference may be excluded from future analysis because it may have resulted from a damaged nucleotide or an amplification error. In some embodiments, a difference in sequence between the TOP and BOT' sequences in a single direct repeat molecule may indicate a sequencing error (e.g., a base mis-call) As such, the present method may identify and eliminate artefactual sequence variations caused by damaged nucleotides, amplification errors and sequencing errors. In some embodiments, the method may comprise amplifying the direct repeat molecules prior to sequencing. As would be apparent from the foregoing discussion, the amplifying is done using primers that hybridize to X and Y, or a complement thereof.

The sequencing step may be done using any convenient next generation sequencing method and may result in at least 10,000, at least 50,000, at least 100,000, at least 500,000, at least 1M at least 10M at least 100M or at least 1B sequence reads. In some cases, the reads are paired-end reads. As would be apparent, the primers used for amplification may be compatible with use in any next generation sequencing platform in which primer extension is used, e.g., Illumina's reversible terminator method, Roche's pyrosequencing method (454), Life Technologies' sequencing by ligation (the SOLiD platform), Life Technologies' Ion Torrent platform or Pacific Biosciences' fluorescent base-cleavage method. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) English (PLoS One. 2012 7: e47768) and Morozova (Genomics. 2008 92:255-64), which are incorporated by reference for the general descriptions of the methods and the particular steps of the methods, including all starting products, reagents, and final products for each of the steps. The sequencing may be done by paired-end sequencing, although single read sequencing can be done in some cases.

The method described above can be employed to analyze genomic DNA from virtually any organism, including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the genomic DNA used in the method may be derived from a mammal, wherein certain embodiments the mammal is a human. In exemplary embodiments, the sample may contain genomic DNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, synovial fluid, urine, amniotic fluid, and semen. In particular embodiments, a sample may be obtained from a subject, e.g., a human. In some embodiments, the sample comprises fragments of human genomic DNA. In some embodiments, the sample may be obtained from a cancer patient. In some embodiments, the sample may be made by extracting fragmented DNA from a patient sample, e.g., a formalin-fixed paraffin embedded tissue sample. In some embodiments, the patient sample may be a sample of cell-free "circulating" DNA from a bodily fluid, e.g., peripheral blood e.g. from the blood of a patient or of a pregnant female. The DNA fragments used in the initial step of the method should be non-amplified DNA that has not been denatured beforehand.

The DNA in the initial sample may be made by extracting genomic DNA from a biological sample, and then fragmenting it. In some embodiments, the fragmenting may be done mechanically (e.g., by sonication, nebulization, or shearing, etc.) or using a double stranded DNA "dsDNA" fragmentase enzyme (New England Biolabs, Ipswich Mass.). In some of these methods (e.g., the mechanical and fragmentase methods), after the DNA is fragmented, the ends may polished and A-tailed prior to ligation to one or more adaptors. Alternatively, the ends may be polished and ligated to adaptors in a blunt-end ligation reaction. In other embodiments, the DNA in the initial sample may already be fragmented (e.g., as is the case for FPET samples and circulating cell-free DNA (cfDNA), e.g., ctDNA). The fragments in the initial sample may have a median size that is below 1 kb (e.g., in the range of 50 bp to 500 bp, or 80 bp to 400 bp), although fragments having a median size outside of this range may be used.

In some embodiments, the amount of DNA in a sample may be limiting. For example, the initial sample of fragmented DNA may contain less than 200 ng of fragmented human DNA, e.g., 1 pg to 20 pg, 10 pg to 200 ng, 100 pg to 200 ng, 1 ng to 200 ng or 5 ng to 50 ng, or less than 10,000 (e.g., less than 5,000, less than 1,000, less than 500, less than 100, less than 10 or less than 1) haploid genome equivalents, depending on the genome.

In some embodiments, sample identifiers (i.e., a sequence that identifies the sample to which the sequence is added, which can identify the patient, or a tissue, etc.) can be added to the polynucleotides prior to sequencing, so that multiple (e.g., at least 2, at least 4, at least 8, at least 16, at least 48, at least 96 or more) samples can be multiplexed. In these embodiments, the sample identifier ligated may be to the initial polynucleotides as part of the asymmetric adaptor, or the sample identifier may be ligated to the polynucleotides in the sub-samples, before or after amplification of those polynucleotides. Alternatively, the tag may be added by primer extension, i.e., using a primer that has a 3' end that hybridizes to an adaptor sequence, and a 5' tail that contains the sample identifier.

The population of direct repeat molecules may be made in a variety of different ways. These methods rely on creating circular molecules, retaining physical proximity between the two strands of one double-stranded DNA molecule, or physically isolating two strands of one double-stranded molecule, during manipulation steps. The methods also divide into strategies requiring one, or more, adaptor types. These methods can be done by fragmenting, polishing and then tailing the ends of the fragments before adaptor ligation. Alternatively, transposases can be used to add adaptor sequences. In some embodiments, standard transposons can be used but then modified to create a Y-shaped adaptor using oligonucleotide replacement (Grunenwald H, Baas B, Goryshin I, Zhang B, Adey A, Hu S, Shendure J, Caruccio N, Maffitt M 2011. Nextera PCR-free DNA library preparation for next-generation sequencing. [Poster presentation, AGBT 2011]; Gertz J, Varley K E, Davis N S, Baas B J, Goryshin I Y, Vaidyanathan R, Kuersten S, Myers R M 2012. Transposase mediated construction of RNA-seq libraries. Genome Res 22: 134-141).

In some embodiments, the direct repeat molecules may be made by (a) ligating adaptor sequences onto both ends of top and bottom strands of a population of fragments double-stranded genomic DNA to produce double-stranded molecules comprising (i) a top strand comprising sequence X at the 5' end and sequence J at the 3' end; and (ii) a bottom strand comprising sequence Y' at the 5' end, and sequence J' at the 3' end; and (b) extending the 3' end of the top strands (i.e., the strand that contains sequence X) using the bottom strand as a template, thereby copying the complement of the bottom strand, as well as sequences J and Y, into the same molecule as the top strand to produce a direct repeat molecule of formula: X-TOP-J-BOT'-Y, wherein: (i) within each repeat molecule TOP and BOT' are amplified from opposite strands of a fragment of the double-stranded of genomic DNA and identical except for positions that correspond to damaged nucleotides in the double-stranded fragment of genomic DNA or amplification errors; (ii) TOP and BOT' vary in the population and have a median length of at least 50 nucleotides; (iii) X and Y are different, non-complementary sequences of at least 10 nucleotides in length that do not vary in the population; and (iv) J is a junction sequence. Examples of this method are shown in the figures and described in greater detail below.

Circularization Methods

Figure 3:
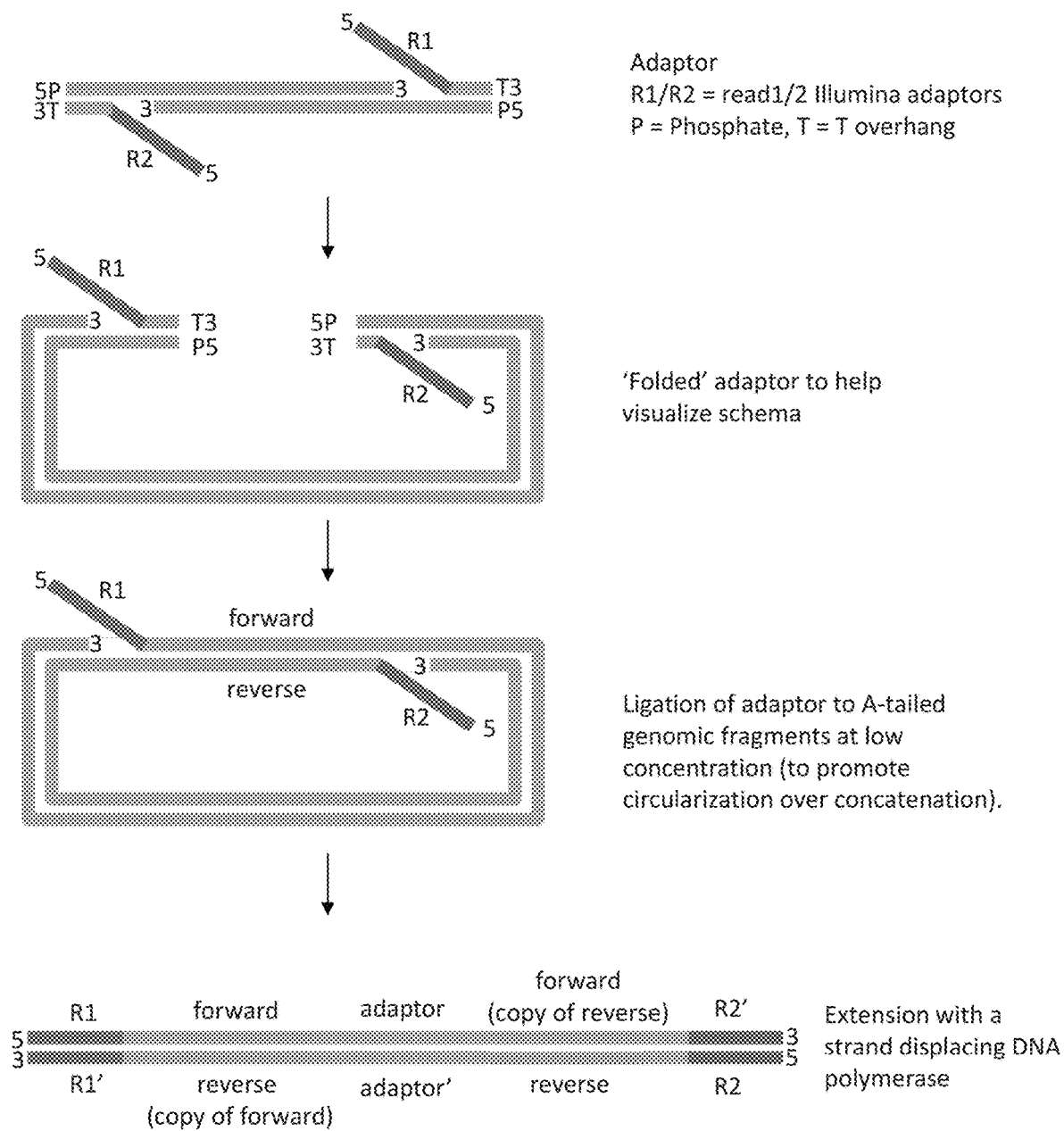
FIG. 3 schematically illustrates an exemplary method by which a population of direct repeat molecules can be produced.
Figure 4:
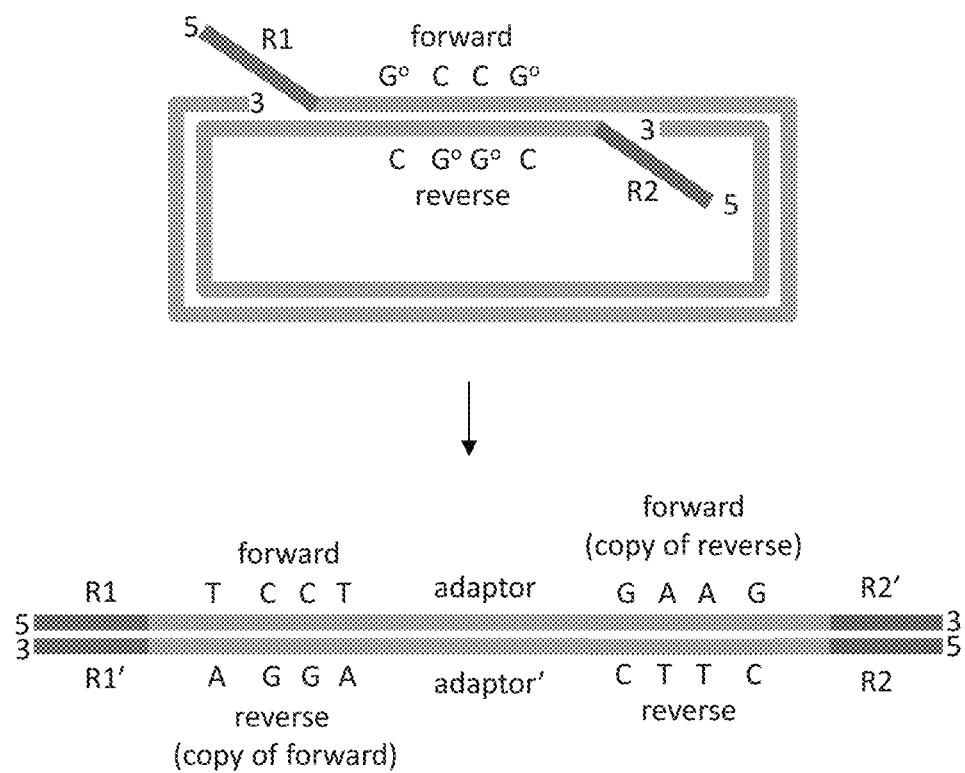
FIG. 4 schematically illustrates how a damaged nucleotide)(G° can be identified using the method illustrated in FIG. 3.

In some embodiments, the direct repeat molecules may be made by ligating a single adaptor onto both ends of top and bottom strands of a population of fragments double-stranded genomic DNA, such that, the individual molecules are in a covalently open circle and, in the individual molecules in the population, sequence X is added onto the 5' end of the top strands of the fragment and sequence Y' is ligated onto the 5' of bottom strands of the fragments. This method involves extending the 3' end of the top strands (i.e., the strand that contains sequence X) using the bottom strand as a template, thereby copying the complement of the bottom strand, as well as sequence Y, into the same molecule as the top strand. Such a molecule can be amplified using primers that have a 3' end that is the same as or that hybridize to sequence X and Y. An example of such a method is illustrated in FIGS. 3 and 4, where the top strand of the fragments of genomic DNA are indicated as "forward" and "reverse" respectively and sequences X and Y' are indicated as sequences R1 and R2. An example of this method is shown in FIGS. 3 and 4.

In some embodiments, the direct repeat molecules may be made by ligating a single adaptor onto both ends of top and bottom strands of a population of fragments double-stranded genomic DNA, such that, the individual molecules are in a covalently closed circle and, in the individual molecules in the population, sequence X is added onto the 5' end of the top strands of the fragment and sequence Y' is ligated onto the 5' of bottom strands of the fragments. This method involves creating one or more nicks by reacting e.g. an adaptor containing dUTP and a mixture UDG/endonuclease IV, extending the 3' end of the top strands (i.e., the strand that contains sequence X) using the bottom strand as a template, thereby copying the complement of the bottom strand, as well as sequence Y, into the same molecule as the top strand. Such a molecule can be amplified using primers that have a 3' end that is the same as or that hybridize to sequence X and Y.

Emulsion PCR

In some embodiments, the direct repeat molecules may be made by isolating adaptor tagged double-stranded molecules are in microdroplets using an emulsion. The emulsion is configured so that the majority of microdroplets contain ≤1 double-stranded DNA molecule i.e. the probability of a microdroplet containing >1 molecule is within reasonable bounds. The adaptor-tagged molecule is then manipulated in the microdroplet to create a direct-repeat.

To reduce the overall number of microdroplets required in the reaction, it is possible to use multiple adaptor sequences. Several double-stranded molecules can then be isolated in a single microdroplet. In this case, the adaptor sequences must be non-compatible. That is, only molecules tagged with the same adaptor sequence can form a direct-repeat, whereas other molecules, with different adaptor sequences, cannot form a direct repeat. In this case, the number of different adaptor sequences and the number of different microdroplets required can be modulated to achieve the desired outcome (e.g. probability of having >1 molecule with the same adaptor sequence in a microdroplet, the total number of microdroplets in the experiment, the desired number of molecules to sequence etc.). An example of this method is shown in FIGS. 5 and 6.

Immobilization

In this approach, the TOP and BOT strands from one double-stranded molecule are immobilised so that they retain proximity to one another. The immobilization can be to a single surface e.g. a streptavidin bead or a microscope slide etc. Alternatively, the immobilization can be between two surfaces e.g. two beads or 2× glass slides separated by a suitable distance. In one, example, beads can be kept a suitable distance from one another by using a 'spacer' oligonucleotide that has both 5' and 3' biotin labels. The spacer would ensure that the beads were within a given distance (as governed by the length of the oligonucleotide). If lots of spacer oligonucleotides were used the beads would form a kind of 'mesh' or hydrogel. Ideally, strands are 5' labelled and immobilised so that their 3' ends are free. The labels would also ideally include spacers to reduce steric hindrance from the solid surface.

Rolling Circle Amplification

Rolling circle amplification cannot be used to generate a direct repeat but can be used to amplify template molecules, whilst keeping Watson and Crick strands from one double-stranded molecule in proximity. For example, a hairpin adaptor can be ligated to both termini of a double-stranded DNA molecule (A flexible and efficient template format for circular consensus sequencing and SNP detection. Travers K J, Chin C S, Rank D R, Eid J S, Turner S W. Nucleic Acids Res. 2010 August; 38(15):e159. doi: 10.1093/nar/gkq543. Epub 2010 Jun. 22. PMID: 20571086). The molecule can then be amplified by hybridising a primer to one, or both, of the hairpin sequences. After amplification, the concatemer RCA product can be digested back to unit length. This digestion can be performed in many different ways. In one example, we can use a restriction endonuclease (although this will cut some genomic DNA sequences). In another example, we can anneal an oligonucleotide to adaptor sequences in the concatemer products. If the oligonucleotide has a modification e.g. a 5methylC then we can specifically digest this sequence, whilst leaving non-methylated genomic DNA untouched. Other modifications/restriction enzyme combinations can be used.

One Adaptor Methods

All of the methods described are workable but have the flaw that all amplicons end up having the same sequence on both 5' ends. This is likely to lead to suppression PCR. Alternatively, after the direct-repeat has been formed, one could ligate a second set of e.g. Y-shaped adaptors to create PCR amplicons that can be amplified without fear of suppression. In this case, the same sequence on the 5' ends can be short thereby reducing the probability of suppression.

Fragmented DNA is ligated using 1× Y-stem adaptor. The single stranded region on the adaptor is A/B'. After ligation and emulsification, a B primer can be used to generate two double-stranded extension products. One has 5'-A-Watson-B'-3'/5'-B-Crick-A'-3 and the other has 5'-A-Crick-B'-3'/5'-B-Watson-A'-3'. At this point the two double-stranded products can be blunt ligated. This is, however, inefficient as the ligation product could be in direct- or inverted-repeat orientations.

Instead, one can use a directional ligation (as shown below). In this case, a B primer can be configured to hybridise internally on the B adaptor sequence thereby creating a C' 3' overhang on each extension product. If the two molecules have complementary overhangs e.g. C'=GATC then the ligation reaction is directional. In an alternative method, suitable overhang sequences can be generated by including cleavable bases in the B extension primer.

One is not limited to Splicing by Overlap Extension (SOEin) reactions could be used. However, in this case the C'/C' sequences may need to be complementary e.g. 5'-GGGGAAAATTTTCCCC-3' (SEQ ID NO: 5).

---

Ligation method 1
Adaptor tagged molecule

5-A-Watson-B'-C'-3
3-C'-B'-Crick-A-5
Denature, extend with 5' phosphorylated B

Note B must be 5' phosphorylated if using ligation
Note C must be self-complementary e.g. 5' GATC
5-A-Watson-B'-C'-3 5-B-Watson-A'-3
3-A'-Crick-B-5 3-C'-B'-Crick-A-5
Ligate 5-A-Watson-B'-C'-B-Watson-A'-3
3-A'-Crick-B-C'-B'-Crick-A-5

---

Ligation method 2
Adaptor tagged molecule

5-A-Watson-B'-3
3-B'-Crick-A-5
Adaptor

5-X-B-3
3-B-X'-5
Denature, hybridise to adaptor

5-A-Watson-B'-3 5-X------B-3
3-B-----X'-5 3-B'-Crick-A-5
Ligate to adaptor

5-A-Watson-B'-X-B-3
3-B-X'-B'-Crick-A-5
Extend

5-A-Watson-B'-X-B-Watson-A'-3
3-A'-Crick-B-X'-B'-Crick-A-5

| Splicing overlap and extension method |
|---|
| Adaptor tagged molecule |
| 5- A-Watson-B'-C'-3<br>3-C'-B'-Crick-A   -5 |
| (Optionally) extend B primer to prevent Watson & Crick re-annealing |
| 5-A-Watson-B'-C'-3     5-   B-Watson-A'-3'<br>3-A'-Crick-B    -5    3-C'-B'-Crick-A -5 |
| (Denature), reanneal |
| Note C' must be self-complementary e.g.<br>5' GGGGAAAATTTTCCCC<br>5-A- Watson-B'-C'-3 (SEQ ID NO: 6)<br>         3'-C'-B'-Crick-A-5 |
| Extend |
| 5-A -Watson-B'-C'-B -Watson-A'-3<br>3-A'-Crick -B -C'-B'-Crick -A -5 |

>1 Adaptor Methods

These methods have the advantage that the final amplicon has different 5' primer sequences thereby allowing direct amplification without the need to undergo a secondary ligation step. However, the disadvantage is that only <100% of molecules will end up with the correct combination of adaptors. For example, if two different adaptor types are used then ~50% of molecules will have the correct combination.

The two strands can be denatured and reannealed. The complementary 3' ends can extend on one another creating strands before being PCR amplified with A and D primers. For SOEin, to provide an efficiency boost, low levels of C/C' primers can be included in the reaction. This will help amplify each of the Watson and Crick strands separately, increasing their effective concentration before the overlap extension reaction at a later PCR cycle. Note that the C/C' primers must have some overlap but that it would be preferable to prevent the overlap being complete (otherwise C/C' will hybridise to each other and not take part in the SOEin reaction). One way to do this is to ensure that the overlap is minimal e.g. 10 bp and a few cycles of PCR at a lower temperature to ensure overlap extension. Also, the relative ratio of A/D vs B/B' primers can be altered to promote generation of a full-length PCR amplicon.

| Ligation method 1 |
|---|
| Adaptor tagged molecule |
| 5-A-Watson-B'-C-3<br>3-C'-B'-Crick-D-5 |
| Denature, extend with 5' phosphorylated B |
| Note B must be 5' phosphorylated if using ligation<br>Note C/C' must be complementary<br>5-A-Watson-B'-C-3 5-B-Watson-D'-3<br>3-A'-Crick-B-5 3-C'-B'-Crick-D-5<br>Ligate |
| 5-A-Watson-B'-C-B-Watson-D'-3<br>3-A'-Crick-B-C'-B'-Crick-D-5 |

| Ligation method 2 |
|---|
| Adaptor tagged molecule |
| 5-A-Watson-B'-3<br>3-B'-Crick-D-5 |
| Adaptor |
| 5- X-B-3<br>3-B-X'-5 |
| Denature, hybridise to adaptor |
| 5-A-Watson-B'-3 5-X------B-3<br>3-B------X'-5 3-B'-Crick-D-5<br>Ligate to adaptor |
| 5-A-Watson-B'-X-B-3<br>3-B-X-B'-Crick-D-5<br>Extend |
| 5-A-Watson-B'-X-B-Watson-D'-3<br>3-A'-Crick-B-X-B'-Crick-D-5<br>Splicing overlap and extension method |
| Adaptor tagged molecule |
| 5-A-Watson-B'-C-3<br>3-C'-B'-Crick-D-5<br>(Optionally) extend B primer to prevent Watson & Crick re-annealing |
| 5-A-Watson-B'-C-3 5-B-Watson-D'-3'<br>3-A'-Crick-B-5 3-C'-B'-Crick-D-5<br>(Denature) reanneal |
| Note C/C' must be complementary<br>5-A-Watson-B'-C-3<br>3'-C'-B'-Crick-A-5<br>or<br>5-A-Watson-B'-C-3 5-B-Watson-D'-3'<br>3-A'-Crick-B-5 3-C'-B'-Crick-D-5<br>Extend |
| 5-A-Watson-B'-C-B-Watson-D'-3<br>3-A'-Crick-B-C'-B'-Crick-D-5 |

Kits

Also provided by this disclosure is a kit for practicing the subject method, as described above. The various components of the kit may be present in separate containers or certain compatible components may be pre-combined into a single container, as desired.

In addition to above-mentioned components, the subject kits may further include instructions for using the components of the kit to practice the subject methods, i.e., to provide instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Utility

As would be readily apparent, the method described above may be employed to analyze any type of sample, including, but not limited to samples that contain heritable mutations, samples that contain somatic mutations, samples from mosaic individuals, pregnant females (in which some of the sample contains DNA from a developing fetus), and samples that contain a mixture of DNA from different sources. In certain embodiments, the method may be used identify a minority variant that, in some cases, may be due to a somatic mutation in a person.

In some embodiments, the method may be employed to detect an oncogenic mutation (which may be a somatic mutation) in, e.g., PIK3CA, NRAS, KRAS, JAK2, HRAS, FGFR3, FGFR1, EGFR, CDK4, BRAF, RET, PGDFRA, KIT or ERBB2, which may be associated with breast cancer, melanoma, renal cancer, endometrial cancer, ovarian cancer, pancreatic cancer, leukemia, colorectal cancer, prostate cancer, mesothelioma, glioma, medullobastoma, polycythemia, lymphoma, sarcoma or multiple myeloma (see, e.g., Chial 2008 Proto-oncogenes to oncogenes to cancer. Nature Education 1:1). Other oncogenic mutations (which may be somatic mutations) of interest include mutations in, e.g., APC, AXIN2, CDH1, GPC3, CYLD, EXT1, EXT2, PTCH, SUFU, FH, SDHB, SDHC, SDHD, VHL, TP53, WT1, STK11/LKB1, PTEN, TSC1, TSC2, CDKN2A, CDK4, RB1, NF1, BMPR1A, MEN1, SMAD4, BHD, HRPT2, NF2, MUTYH, ATM, BLM, BRCA1, BRCA2, FANCA, FANCC, FANCD2, FANCE, FANCF, FANCG, NBS1, RECQL4, WRN, MSH2, MLH1, MSH6, PMS2, XPA, XPC, ERCC2-5, DDB2 or MET, which may be associated with colon, thyroid, parathyroid, pituitary, islet cell, stomach, intestinal, embryonal, bone, renal, breast, brain, ovarian, pancreatic, uterine, eye, hair follicle, blood or uterus cancers, pilotrichomas, medulloblastomas, leiomyomas, paragangliomas, pheochromocytomas, hamartomas, gliomas, fibromas, neuromas, lymphomas or melanomas. In some embodiments, the method may be employed to detect a somatic mutation in genes that are implicated in cancer, e.g., CTNNB1, BCL2, TNFRSF6/FAS, BAX, FBXW7/CDC4, GLI, HPVE6, MDM2, NOTCH1, AKT2, FOXO1A, FOXO3A, CCND1, HPVE7, TALL TFE3, ABL1, ALK, EPHB2, FES, FGFR2, FLT3, FLT4, KRAS2, NTRK1, NTRK3, PDGFB, PDGFRB, EWSR1, RUNX1, SMAD2, TGFBR1, TGFBR2, BCL6, EVI1, HMGA2, HOXA9, HOXA11, HOXA13, HOXC13, HOXD11, HOXD13, HOX11, HOX11L2, MAP2K4, MLL, MYC, MYCN, MYCL1, PTNP1, PTNP11, RARA, SS18 (see, e.g., Vogelstein and Kinzler 2004 Cancer genes and the pathways they control. Nature Medicine 10:789-799). The method of embodiment may be employed to detect any somatic mutation that is implicated in cancer which is catalogued by COSMIC (Catalogue of Somatic Mutations in Cancer), data of which can be accessed on the internet.

Other mutations of interest include mutations in, e.g., ARID1A, ARID1B, SMARCA4, SMARCB1, SMARCE1, AKT1, ACTB/ACTG1, CHD7, ANKRD11, SETBP1, MLL2, ASXL1, which may be at least associated with rare syndromes such as Coffin-Siris syndrome, Proteus syndrome, Baraitser-Winter syndrome, CHARGE syndrome, KBG syndrome, Schinzel-Giedion syndrome, Kabuki syndrome or Bohring-Opitz syndrome (see, e.g., Veltman and Brunner 2012 De novo mutations in human genetic disease. Nature Reviews Genetics 13:565-575). Hence, the method may be employed to detect a mutation in those genes.

In other embodiments, the method may be employed to detect a mutation in genes that are implicated in a variety of neurodevelopmental disorders, e.g., KAT6B, THRA, EZH2, SRCAP, CSF1R, TRPV3, DNMT1, EFTUD2, SMAD4, LIS1, DCX, which may be associated with Ohdo syndrome, hypothyroidism, Genitopatellar syndrome, Weaver syndrome, Floating-Harbor syndrome, hereditary diffuse leukoencephalopathy with spheroids, Olmsted syndrome, ADCA-DN (autosomal-dominant cerebellar ataxia, deafness and narcolepsy), mandibulofacial dysostosis with microcephaly or Myhre syndrome (see, e.g., Ku et al 2012 A new paradigm emerges from study of de novo mutations in the context of neurodevelopmental disease. Molecular Psychiatry 18:141-153). The method may also be employed to detect a somatic mutation in genes that are implicated in a variety of neurological and neurodegenerative disorders, e.g., SCN1A, MECP2, IKBKG/NEMO or PRNP (see, e.g., Poduri et al 2014 Somatic mutation, genetic variation, and neurological disease. Science 341(6141):1237758).

In some embodiments, a sample may be collected from a patient at a first location, e.g., in a clinical setting such as in a hospital or at a doctor's office, and the sample may be forwarded to a second location, e.g., a laboratory where it is processed and the above-described method is performed to generate a report. A "report" as described herein, is an electronic or tangible document which includes report elements that provide test results that may indicate the presence and/or quantity of minority variant(s) in the sample. Once generated, the report may be forwarded to another location (which may be the same location as the first location), where it may be interpreted by a health professional (e.g., a clinician, a laboratory technician, or a physician such as an oncologist, surgeon, pathologist or virologist), as part of a clinical decision.

The method may be used to analyze diseases that are associated with mutations, transplant rejection and has applications in non-invasive prenatal testing.

EMBODIMENTS

Embodiment 1

A population of direct repeat molecules having a strand of the formula: X-TOP-J-BOT'-Y, wherein: (i) within each repeat molecule TOP and BOT' are amplified from opposite strands of a double-stranded fragment of genomic DNA and are identical except for positions that correspond to damaged nucleotides in the double-stranded fragment of genomic DNA or errors that occur during amplification; (ii) TOP and BOT' vary in the population and have a median length of at least 50 nucleotides; (iii) X and Y are different, non-complementary sequences of at least 10 nucleotides in length that do not vary in the population; and (iv) J is a junction sequence.

Embodiment 2

The population of direct repeat molecules of embodiment 1, wherein, in the population, TOP and BOT' each have a complexity of at least 103.

Embodiment 3

The population of direct repeat molecules of any prior embodiment, wherein the population of direct repeat molecules have a strand of the formula 5'-X-(T)TOP(A)-J-(T)BOT'(A)-Y-3', wherein (T) and (A) are thymine and adenine nucleotides that are immediately adjacent to TOP and BOT'.

Embodiment 4

The population of direct repeat molecules of any prior embodiment, wherein the direct repeat molecules are double-stranded.

Embodiment 5

The population of direct repeat molecules of any prior embodiment, wherein the genomic DNA is eukaryotic genomic DNA.

Embodiment 6

The population of direct repeat molecules of embodiment 5, wherein the genomic DNA is isolated from a tissue biopsy.

Embodiment 7

The population of direct repeat molecules of embodiment 5, wherein the genomic DNA is cell-free DNA (cfDNA).

Embodiment 8

The population of direct repeat molecules of any of embodiments 1-4, wherein the genomic DNA is microbial genomic DNA.

Embodiment 9

The population of direct repeat molecules of any of embodiments 1-4, wherein the genomic DNA is viral genomic DNA.

Embodiment 10

The population of direct repeat molecules of any prior embodiment, wherein TOP and BOT' have a median length of less than 2,000 nucleotides.

Embodiment 11

The population of direct repeat molecules of any prior embodiment, wherein the molecules are free in solution.

Embodiment 12

The population of direct repeat molecules of any prior embodiment, wherein J is at least 10 nucleotides in length.

Embodiment 13

The population of direct repeat molecules of any prior embodiment, wherein J varies in the population.

Embodiment 14

The population of direct repeat molecules of any prior embodiment, further comprising one or more molecular barcodes.

Embodiment 15

A method of sequencing, comprising:

sequencing a population of direct repeat molecules of any of embodiments 1-14 to obtain the sequences of TOP and BOT' from the same molecule; and comparing the sequences of TOP and BOT' from the same molecule to determine if they are the same or different.

Embodiment 16

The method of embodiment 15, further comprising identifying a difference in the sequences of TOP and BOT' from the same molecule.

Embodiment 17

The method of embodiment 16, further comprising excluding the base calls corresponding to a sequence difference from future analysis.

Embodiment 18

The method of any of embodiments 15-17, wherein the method comprises, prior to sequencing, amplifying the direct repeat molecules.

Embodiment 19

The method of embodiment 18, wherein the amplifying is done using primers that hybridize to X and Y, or a complement thereof.

Embodiment 20

The method of any of embodiments 15-19, wherein the sequencing is done by paired end sequencing.

Embodiment 21

A method for making a population of direct repeat molecules of embodiment 1, comprising: (a) ligating adaptor sequences onto both ends of top and bottom strands of a population of fragments double-stranded genomic DNA to produce double-stranded molecules comprising: (i) a top strand comprising sequence X at the 5' end and sequence J at the 3' end; and (ii) a bottom strand comprising sequence Y' at the 5' end, and sequence J' at the 3' end; and (b) extending the 3' end of the top strands using the bottom strands as a template, thereby adding the complement of the bottom strands and sequence Y onto the end 3' end of the top strands.

EXAMPLES

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Methods

Adaptor sequences are shown in FIG. 8. Three i7 indexes were pooled (D701, D702, D704) to maintain color balance for each base of the index read being sequenced, otherwise index read sequencing could fail due to registration failure (see Nextera Low Plex Pooling Guidelines). To prepare double-stranded adaptor I re-suspended each oligonucleotide at 100 µM in nuclease-free duplex buffer (IDT, 30 mM HEPES, pH 7.5, 100 mM Potassium Acetate). For each adaptor, equal amounts of each of the four oligonucleotides were mixed, heated to 95° C. 2 min and then cooled at −0.1° C./sec to 4° C. I then pooled equal volumes of each of the three adaptors (with different i7 indexes). Adaptors were diluted to 0.06 µM (3.1×) and 0.018 µM (1×).

Store bought genomic DNA (Promega) was sheared by Covaris to a peak size of ~150 bp. Fragmented DNA was then end-repaired using the NEB UltraII kit. Briefly, 1 µg fragmented DNA was added to a reaction including 7 µL UltraII end prep reaction buffer, 3 µL UltraII end prep enzyme mix and made up to 60 µL with T0.1E. The reaction was incubated at 20° C. 30 mins, 65° C. 30 mins before a 4° C. hold. The end-repaired DNA was 1× AMPure XP purified and quantitated by Qubit HS kit at 8.88 ng/µL.

Ligation reactions included ~3 nM template, equivalent to 1.83 µL end-repaired template (16.25 ng total), 10 µL adaptors (either 3.1× or 1×), 6 µL 10×T4 DNA ligase buffer, 0.9 µL T4 DNA ligase (400 U/µL) and 41.27 µL dH2O to give 60 µL total volume. The reaction was incubated for 14° C. 2 hours then stored at 4° C. In total 8 reactions were setup, 4× with 3.1× excess adaptor and 4× with 1× excess adaptor. Ligation reactions with the same adaptor concentration were pooled together (4×60 µL), purified by 1× AMPure XP and eluted in 88 µL dH2O.

PCR reactions included 5 µL 10× Thermopol buffer, 2 µL 10 mM dNTPs, 0.4 µL D5 primer (100 µM), 0.4 µL i7 no MID primer (100 µM), 1 µL DeepVent exo− or DeepVent exo+, 20.6 µL AMPure XP purified sample and 20.6 µL dH2O to give a 50 µL reaction. Reactions were incubated at 72° C. 5 min then 12× cycles of 98° C. 30 sec, 60° C. 30 sec, 72° C. 5 min; then 72° C. 5 min and a 4° C. store. Duplicate PCR reactions were performed for each sample, each duplicate with different i5 primers. PCR primer sequences are given in Table 1 below.

TABLE 1

Primer sequences.

| Primer | Sequence 5'>3' |
|---|---|
| D501 | AATGATACGGCGACCACCGAGATCTACAC<u>TATAGCCT</u>ACACTC TTTCCCTACACGA\*C (SEQ ID NO: 7) |
| D502 | AATGATACGGCGACCACCGAGATCTACAC<u>ATAGAGGC</u>ACACTC TTTCCCTACACGA\*C (SEQ ID NO: 8) |
| D503 | AATGATACGGCGACCACCGAGATCTACAC<u>CCTATCCT</u>ACACTC TTTCCCTACACGA\*C (SEQ ID NO: 9) |
| D605 | AATGATACGGCGACCACCGAGATCTACAC<u>GGCTCTGA</u>ACACTC TTTCCCTACACGA\*C (SEQ ID NO: 10) |
| i7 | CAAGCAGAAGACGGCATACGAGAT<u>*GTGACTGGAGTTCAGACGT G*</u>\**T* (SEQ ID NO: 11) |

Underline = i5 index sequence, bold = read 1, underlined and italics = read 2, asterisk = phosphorothioate linkage.

Duplicate PCR reactions were pooled (2×50 µL), purified by 0.5× AMPure XP and eluted in 30 µL dH2O. Reactions, including no template controls, were quantitated by Qubit HS kit, and analysed by Bioanalyzer. Reactions were pooled in a ratio of 0.4:0.4:0.1:0.1 3.1× exo−: 3.1× exo+: 1× exo−: 1× exo+ and sequenced using an Illumina MiSeq. Custom primers for the i7 index read and read 2 were used (Table 2). Standard Illumina primers were used for i5 index read and read 1.

TABLE 2

Primer sequences.

| Primer | Sequence 5'>3' |
|---|---|
| Multiplexing read 2 sequencing primer | GTGACTGGAGTTCAGACGTGTACCTGTCCTTCCT\*T (SEQ ID NO: 12) |
| i7 index read | ATGAAACAATCATCTAAATCACGTGTGATCAGGGT\*C (SEQ ID NO: 13) |

Asterisk = phosphorothioate linkage.

Results

Chimeras

In initial proof of concept experiments, a synthetic oligonucleotide substrate of defined length was used and identified a significant proportion of PCR amplicons had length consistent with one, rather than two, insert sequences. The hypothesis is that these amplicons derived from PCR recombination, which was exacerbated by the low molecular complexity (only one oligonucleotide substrate in the experiment). Conditions to reduce PCR recombination were developed, with best results from increasing both the PCR extension time and primer concentration. The same PCR conditions were applied to the genomic DNA library and also used a 0.5× AMPure XP step to remove smaller PCR amplicons, although the Bioanalyzer traces suggest that this had variable success (FIG. 9). For example, lower fragment lengths 300-500 bp are observed in the 3.1× DeepVent exo+ reaction.

PCR recombination is a concern in DRSeq since, in theory, it may be difficult to distinguish amplicons with direct-repeats from chimeras with only one insert sequence (both map as properly paired reads). To distinguish between these possibilities, the i7 index read was positioned within the adaptor sequence (FIG. 7). PCR recombination events that remove one of the direct-repeats also remove the i7 index sequence, whereas bona fide direct-repeat amplicons contain the i7 index sequence. The number of demultiplexed reads with both i5 and i7 sequences was counted and compared this to the number of reads in the MiSeq Undetermined folder with an i5 index but no matching i7 index (matching was defined as an index sequence with a Levenshtein edit distance of <3). Results in Table 3 show that chimeric rates were increased for DeepVent exo+ compared to DeepVent exo− consistent with previous observations of recombination rates for these enzymes (Potapov & Ong. Examining Sources of Error in PCR by Single-Molecule Sequencing. PLoS One. 12(1):e0169774 (2017)).

TABLE 3

Counts of read with i7 indexes matching/mismatching known index sequences.

| Adaptor | DeepVent exo | Demuxed (i5 & i7) | Unindexed (i5 only) | Total reads | % reads with i7 index |
|---|---|---|---|---|---|
| 3.1× | − | 3,816,569 | 811,345 | 4,627,914 | 82.47% |
| 3.1× | + | 4,023,314 | 1,911,034 | 5,934,348 | 67.80% |
| 1× | − | 863,087 | 105,482 | 968,569 | 89.11% |
| 1× | + | 372,742 | 224,427 | 597,169 | 62.42% |

Analysis of sequencing data showed that DeepVent exo+ and exo− had a similar percentage of properly paired reads, albeit at a lower percentage than a typical NGS experiment, suggesting that the majority of adaptor ligation events were intramolecular (Table 4).

TABLE 4

Rates of properly paired reads.

| Adaptor | DeepVent exo | Paired in sequencing | Properly paired | % properly paired |
|---|---|---|---|---|
| 3.1x | − | 3,699,840 | 3,080,952 | 83.27% |
| 3.1x | + | 3,946,464 | 3,476,282 | 88.09% |
| 1x | − | 841,552 | 746,760 | 88.74% |
| 1x | + | 362,082 | 316,956 | 87.54% |

Overlap

The orientation of the reads in the final direct-repeat amplicon is configurable (we could sequence both direct repeats in the same orientation [as per duplex sequencing], both direct repeats in different orientations [analogous to overlapping reads], or both direct repeats in both orientations [requiring 4× reads per fragment]). In the current setup, one forward and one reverse read was used to call overlapping bases. Overall, 58-68% bases were overlapping (Table 5). The mean template length of fragments was slightly longer than the optimum 150 bp, suggesting that shearing conditions could be optimized further.

TABLE 5

Overlap metrics. Total bases equals number of reads × 150. Overlapping bases: number of reads with a tlen × length of overlap, where length of overlap equals max(0, min(tlen, 150) − max(0, tlen − 150)). No base or read quality filters were applied.

| Adaptor | Deep Vent exo | Mean tlen | Overlapping bases | Total bases | % bases overlapping |
|---|---|---|---|---|---|
| 3.1x | − | 193.96 | 136,016,034 | 199,124,550 | 68.31% |
| 3.1x | + | 198.36 | 151,827,785 | 234,243,150 | 64.82% |
| 1x | − | 210.48 | 29,151,076 | 49,860,000 | 58.47% |
| 1x | + | 190.97 | 14,771,848 | 21,493,650 | 68.73% |

Error Profiles

The fraction of overlapping calls that were mismatches was $6.77 \times 10^{-4}$ and $6.99 \times 10^{-4}$ for DeepVent exo- and $1.36 \times 10^{-4}$ and $1.55 \times 10^{-4}$ for DeepVent exo+ (restricted to base quality Q≥30, non-duplicate, properly paired reads). This demonstrates that we could detect differences in the error-rates of DeepVent exo+ and exo-, using the overlap between one read-pair (no PCR duplicates) and in the presence of NGS errors.

TABLE 6

Calls were made if both overlapping bases had base qualities Q ≥ 30.

| Adaptor | DeepVent exo | Mismatches | Total | Proportion mismatched |
|---|---|---|---|---|
| 3.1x | − | 84.078 | 124,220,132 | $6.77 \times 10^{-4}$ |
| 3.1x | + | 19.253 | 141,289,421 | $1.36 \times 10^{-4}$ |
| 1x | − | 18.306 | 26,194,273 | $6.99 \times 10^{-4}$ |
| 1x | + | 2.132 | 13,790,705 | $1.55 \times 10^{-4}$ |

To compare the error profiles of DeepVent exo- and DeepVent exo+ the counts of errors was normalized to the total number of overlapping calls (FIG. 10). Assuming that the reference base was correct, which allowed errors to be assigned to one strand and e.g. GC>TA errors separated into G>T and C>A errors. Visually, there was no bias between errors assigned to the forward or reverse strand, therefore these were summed together. Reassuringly, DeepVent exo+ had a higher proportion of G>T than C>A errors, consistent with 8-oxoguanine damage. The higher rates of G>T compared to C>A was present, but reduced, for DeepVent exo-. Compared to DeepVent exo+, DeepVent exo- had an elevated proportion of A>T errors, consistent with previous results (18% exo- versus <5% exo+, Popapov & Ong, 2017).

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A population of direct repeat molecules having a strand of the formula:

X-TOP-J-BOT'-Y, wherein:

(i) each direct repeat molecule contains one copy of TOP and one copy of BOT' and within each repeat molecule TOP and BOT' are amplified from opposite strands of a double-stranded fragment of genomic DNA and are identical except for positions that correspond to damaged nucleotides in the double-stranded fragment of genomic DNA or errors that occur during amplification;

(ii) TOP and BOT' vary in the population and have a median length of at least 50 nucleotides;

(iii) X and Y are different, non-complementary sequences of at least 10 nucleotides in length that do not vary in the population; and (iv) J is a junction sequence.

2. The population of direct repeat molecules of claim 1, wherein, in the population, TOP and BOT' each have a complexity of at least $10^3$.

3. The population of direct repeat molecules of claim 1, wherein the population of direct repeat molecules have a strand of the formula

X-(T)TOP(A)-J-(T)BOT'(A)-Y, wherein (T) and (A) are thymine and adenine nucleotides that are immediately adjacent to TOP and BOT'.

4. The population of direct repeat molecules of claim 1, wherein the direct repeat molecules are double-stranded.

5. The population of direct repeat molecules of claim 1, wherein the genomic DNA is eukaryotic genomic DNA.

6. The population of direct repeat molecules of claim 5, wherein the genomic DNA is isolated from a tissue biopsy.

7. The population of direct repeat molecules of claim 5, wherein the genomic DNA is cell-free DNA (cfDNA).

8. The population of direct repeat molecules of claim 1, wherein the genomic DNA is microbial genomic DNA.

9. The population of direct repeat molecules of claim 1, wherein the genomic DNA is viral genomic DNA.

10. The population of direct repeat molecules of claim 1, wherein TOP and BOT' have a median length of less than 2,000 nucleotides.

11. The population of direct repeat molecules of claim 1, wherein the molecules are free in solution.

12. The population of direct repeat molecules of claim 1, wherein J is at least 10 nucleotides in length.

13. The population of direct repeat molecules of claim 1, wherein J varies in the population.

14. The population of direct repeat molecules of claim 1, further comprising one or more molecular barcodes.

15. A method of sequencing, comprising:

(a) producing a population of direct repeat molecules of claim 1 by:

(i) ligating adaptor sequences onto both ends of top and bottom strands of a population of fragments double-stranded genomic DNA to produce double-stranded molecules comprising:

a top strand comprising sequence X at the 5' end and sequence J at the 3' end; and a bottom strand comprising sequence Y' at the 5' end, and sequence J' at the 3' end; and (ii) extending the 3' end of the top strands using the bottom strands as a template, thereby adding the complement of the bottom strands and sequence Y onto the end 3' end of the top strands;

(b) sequencing the population of direct repeat molecules of claim 1 to obtain the sequences of TOP and BOT' from the same molecule; and (c) comparing the sequences of TOP and BOT' from the same molecule to determine if they are the same or different.

16. The method of claim 15, further comprising identifying a difference in the sequences of TOP and BOT' from the same molecule.

17. The method of claim 16, further comprising excluding the base calls corresponding to a sequence difference from future analysis.

18. The method of claim 15, wherein the method comprises, prior to sequencing, amplifying the direct repeat molecules.

19. The method of claim 18, wherein the amplifying is done using primers that hybridize to X and Y, or a complement thereof.

20. The method of claim 15, wherein the sequencing is done by paired end sequencing.

21. A method for making a population of direct repeat molecules of claim 1, comprising:

(a) ligating adaptor sequences onto both ends of top and bottom strands of a population of fragments double-stranded genomic DNA to produce double-stranded molecules comprising:
  (i) a top strand comprising sequence X at the 5' end and sequence J at the 3' end; and
  (ii) a bottom strand comprising sequence Y' at the 5' end, and sequence J' at the 3' end; and
(b) extending the 3' end of the top strands using the bottom strands as a template, thereby adding the complement of the bottom strands and sequence Y onto the end 3' end of the top strands.

\* \* \* \* \*

UNITED STATES PATENT AND TRADEMARK OFFICE
CERTIFICATE OF CORRECTION

PATENT NO. : 11,078,482 B2  
APPLICATION NO. : 16/622838  
DATED : August 3, 2021  
INVENTOR(S) : Robert Osborne et al.

Page 1 of 1

It is certified that error appears in the above-identified patent and that said Letters Patent is hereby corrected as shown below:

In the Claims

In Column 36, Line 46, please delete "of Claim 1".

Signed and Sealed this  
Twenty-third Day of November, 2021

Drew Hirshfeld  
*Performing the Functions and Duties of the*  
*Under Secretary of Commerce for Intellectual Property and*  
*Director of the United States Patent and Trademark Office*